United States Patent
Buder et al.

(10) Patent No.: US 9,895,289 B2
(45) Date of Patent: Feb. 20, 2018

(54) MIXING SYRINGE

(71) Applicant: Covidien LP, Mansfield, MA (US)

(72) Inventors: Christopher Buder, Sharon, MA (US); Andrew Koss, Middleboro, MA (US); Anastasia Righter, Milford, MA (US)

(73) Assignee: Covidien LP, Mansfield, MA (US)

( * ) Notice: Subject to any disclaimer, the term of this patent is extended or adjusted under 35 U.S.C. 154(b) by 91 days.

(21) Appl. No.: 14/687,079

(22) Filed: Apr. 15, 2015

(65) Prior Publication Data

US 2015/0297457 A1 Oct. 22, 2015

Related U.S. Application Data (60) Provisional application No. 61/981,354, filed on Apr. 18, 2014.

(51) Int. Cl.
*B65D 88/54* (2006.01)
*G01F 13/00* (2006.01)
(Continued)

(52) U.S. Cl.
CPC ....... *A61J 1/2093* (2013.01); *A61B 17/12031* (2013.01); *A61B 17/12186* (2013.01);
(Continued)

(58) Field of Classification Search
CPC . A61J 1/2093; A61J 1/2003; A61B 17/12031; A61B 17/12186;
(Continued)

(56) References Cited

U.S. PATENT DOCUMENTS 2,708,438 A * 5/1955 Cohen ................... A61M 5/284
604/192
3,927,868 A 12/1975 Moore
(Continued)

FOREIGN PATENT DOCUMENTS

EP 2111918 A2 10/2009
EP 2145599 A1 1/2010
(Continued)

OTHER PUBLICATIONS

"Head" Merriam-Webster.com. Merriam-Webster, Nov. 2016.*
(Continued)

*Primary Examiner* — Benjamin R Shaw
(74) *Attorney, Agent, or Firm* — Shumaker & Sieffert, P.A.

(57) ABSTRACT

In some examples, a mixing syringe includes a fluid housing defining an internal housing chamber for storing a medical agent, and a fluid outlet. An outer plunger is disposed within the internal housing chamber of the fluid housing. The outer plunger includes an outer barrel defining a barrel cavity and an outer plunger head connected to the outer barrel. The outer plunger is adapted for longitudinal movement within the internal housing chamber of the fluid housing. The outer plunger head defines a flow passage whereby, upon movement of the outer plunger the medical agent passes from the internal housing chamber through the flow passage into the barrel cavity of the outer plunger. An inner plunger is adapted for longitudinal movement relative to the outer plunger to force the medical agent through the flow passage of the outer plunger head for disposition through the fluid outlet of the fluid housing.

22 Claims, 9 Drawing Sheets

(51) Int. Cl.
*A61J 1/20* (2006.01)
*A61B 17/12* (2006.01)
*A61M 5/00* (2006.01)
*A61B 17/00* (2006.01)

(52) U.S. Cl.
CPC ............ *A61J 1/2003* (2015.05); *A61M 5/007* (2013.01); *A61B 17/00491* (2013.01); *A61B 2017/00526* (2013.01); *A61B 2017/1205* (2013.01); *A61M 2207/00* (2013.01)

(58) Field of Classification Search
CPC ..... A61B 17/00491; A61B 2017/1205; A61M 5/007; A61M 2005/31598; A61M 3/005; A61M 5/31501; A61M 5/31505; A61M 2005/31506; A61C 5/062; B65D 81/3211
USPC .............. 222/252, 145.5, 145.1; 433/89, 90; 366/602, 130; 206/538, 219, 221; 215/DIG. 8; 604/82, 89, 416, 220
See application file for complete search history.

(56) References Cited

U.S. PATENT DOCUMENTS

| | | | |
|---|---|---|---|
| 4,040,420 A | 8/1977 | Speer | |
| 4,204,775 A | 5/1980 | Speer | |
| 4,261,481 A | 4/1981 | Speer | |
| 4,583,978 A * | 4/1986 | Porat | A61M 5/31511 604/208 |
| 5,116,315 A | 5/1992 | Capozzi et al. | |
| 5,318,547 A * | 6/1994 | Altschuler | A61M 5/315 604/198 |
| 5,512,054 A * | 4/1996 | Morningstar | A61M 5/3129 604/191 |
| 5,531,710 A * | 7/1996 | Dang | A61M 5/178 215/355 |
| 5,580,568 A | 12/1996 | Greff et al. | |
| 5,630,800 A * | 5/1997 | Blank | A61M 5/31596 604/228 |
| 5,667,767 A | 9/1997 | Greff et al. | |
| 5,694,480 A | 12/1997 | Itakura | |
| 5,851,508 A | 12/1998 | Greff et al. | |
| 6,033,427 A | 3/2000 | Lee | |
| 6,386,872 B1 * | 5/2002 | Mukasa | A61O 5/064 206/219 |
| 6,511,472 B1 * | 1/2003 | Hayman | A61M 25/0097 604/533 |
| 7,018,089 B2 * | 3/2006 | Wenz | A61M 5/31511 206/219 |
| 9,326,829 B2 * | 5/2016 | Kojima | A61C 5/062 |
| 2005/0177100 A1 * | 8/2005 | Harper | A61M 5/31596 604/89 |
| 2006/0071025 A1 * | 4/2006 | Crews | |
| 2006/0173415 A1 * | 8/2006 | Cummins | A61M 5/31505 604/181 |
| 2009/0118703 A1 * | 5/2009 | Orilla | A61F 9/0017 604/521 |
| 2009/0247985 A1 | 10/2009 | Melsheimer et al. | |
| 2010/0049165 A1 * | 2/2010 | Sutherland | A61M 25/0069 604/508 |
| 2010/0100099 A1 * | 4/2010 | Reilly | A61B 17/8822 606/93 |
| 2010/0305514 A1 * | 12/2010 | Valenti | A61F 9/0017 604/239 |
| 2011/0027751 A1 * | 2/2011 | Kojima | A61O 5/064 433/90 |
| 2011/0121035 A1 | 5/2011 | Greter et al. | |
| 2011/0139821 A1 | 6/2011 | Greter et al. | |
| 2013/0126559 A1 * | 5/2013 | Cowan | A61M 5/31525 222/333 |
| 2013/0269806 A1 | 10/2013 | Burns | |
| 2013/0338643 A1 * | 12/2013 | De Silva | A61B 17/12113 604/533 |
| 2014/0048556 A1 | 2/2014 | Pearcy et al. | |
| 2014/0257233 A1 * | 9/2014 | Cowan | A61M 5/31563 604/500 |
| 2016/0296703 A1 * | 10/2016 | Bailey | A61M 5/2448 |

FOREIGN PATENT DOCUMENTS

| | | |
|---|---|---|
| JP | 2002282368 | 10/2002 |
| WO | 0187389 A1 | 11/2001 |
| WO | 0205898 A1 | 1/2002 |
| WO | 03039375 A2 | 5/2003 |
| WO | 2004047651 A2 | 6/2004 |
| WO | 2005048977 A2 | 6/2005 |
| WO | 2007089948 A2 | 8/2007 |

OTHER PUBLICATIONS

"Connected" Merriam-Webster.com. Merriam-Webster, Nov. 2016.*
International Search Report and Written Opinion from counterpart International Application No. PCT/US2015/025846, dated Sep. 3, 2015, 11 pp.
U.S. Appl. No. 14/687,246, by Christopher Buder, filed Apr. 15, 2015.
Response to Communication Pursuant to Rules 161(1) and 162 EPC dated May 24, 2017 from counterpart European Application No. 15718410.2-1654, 43 pp.
Communication Pursuant to Rules 161(1) and 162 EPC dated Nov. 25, 2016 from counterpart European Application No. 15718410.2-1654, 2 pp.
International Preliminary Report on Patentability from International Application No. PCT/US2015/025846, dated Oct. 18, 2016, 7 pp.

* cited by examiner

MIXING SYRINGE

This application claims the benefit of U.S. Provisional Patent Application No. 61/981,354, which was filed on Apr. 18, 2014 and is entitled, "MIXING SYRINGE," the entire content of which is incorporated herein by reference.

TECHNICAL FIELD

The present disclosure relates to a mixing syringe, and, in particular, relates to a mixing syringe used to deliver liquid embolic compositions for the embolization of blood vessels.

BACKGROUND

The delivery of fluid compositions which solidify in vivo is useful for numerous vascular applications including the occlusion of neurovascular aneurysms, arteriovenous malformations ("AVMs"), arteriovenous fistulas ("AVF"), abdominal aortic aneurysm Type 1 and Type 2 endoleaks, bleeding, tumors (including hypervascular tumors), varicose seals, and portal vein embolization, as well as in the sterilization of mammals and the treatment of urinary incontinence. Some liquid embolic compositions include a water insoluble, biocompatible, non-biodegradable polymer, dissolved in biocompatible solvent. These liquid embolic compositions can include a water insoluble, radiopaque material or contrast agent to permit the clinician to visualize delivery of the composition to the vascular treatment site via conventional techniques such as fluoroscopy.

Liquid embolic compositions may be delivered via a catheter technique that permits the clinician to selectively place the catheter at any desired location within the vasculature. A catheter tip is directed to the desired location by use of a visualization technique, such as fluoroscopy. The liquid embolic composition is delivered to the catheter through a syringe connected to the catheter hub. Some current practices require the liquid embolic composition to be continuously mixed for 20 minutes in a vial to achieve adequate suspension of the contrast agent during delivery. Inadequate mixing or delays in delivery after mixing may result in contrast agent settling, causing poor visualization of the liquid embolic composition during injection. Accurate visualization helps ensure that the liquid embolic composition is being delivered to the intended vascular site, to detect undesired reflux of the liquid embolic composition on the catheter tip, or to detect premature solidification of the liquid embolic composition causing catheter or branch vessel occlusion.

SUMMARY

The present disclosure describes a mixing syringe comprising a fluid housing defining an internal housing chamber and a fluid outlet in communication with the internal housing chamber. The mixing syringe further comprises an outer plunger disposed within the internal housing chamber of the fluid housing. The outer plunger defines a cavity and comprises an outer plunger head defining a flow passage between the cavity and the internal housing chamber. The outer plunger is configured to move relative to the fluid housing between a proximal position and a distal position. The mixing syringe further comprises an inner plunger at least partially disposed within the cavity defined by the outer plunger. The inner plunger is configured to move between a retracted position and an advanced position relative to the outer plunger. When the outer plunger is in the distal position and fluid is disposed in the cavity of the outer plunger, movement of the inner plunger toward the advanced position causes the inner plunger to force the fluid through the flow passage of the outer plunger head and through the fluid outlet of the fluid housing.

In some embodiments, the outer plunger comprises an outer barrel defining the cavity, and the outer plunger head is connected to the outer barrel. In addition, in some embodiments, the inner plunger comprises an inner plunger barrel and an inner plunger head connected to the inner plunger barrel.

In some embodiments, the outer plunger head is configured to rotate within the internal housing chamber of the fluid housing. In some embodiments, the outer plunger head includes at least one scraper element dimensioned to contact an inner housing wall of the fluid housing during rotational movement thereof. The at least one scraper element may be dimensioned to extend to an outer periphery of the outer plunger head. In embodiments, the outer plunger head includes a plurality of scraper elements.

In some embodiments, the outer plunger head is dimensioned to establish a substantial fluid tight seal with the inner housing wall of the fluid housing. In certain embodiments, the inner plunger head is dimensioned to establish a substantial fluid tight seal with an inner barrel wall of the outer plunger.

In some embodiments, a fluid is disposed within the internal housing chamber. In some embodiments, the fluid may be a liquid embolic composition including a contrast agent. The contrast agent may be water insoluble. In some embodiments, the contrast agent may be one of tantalum, tantalum oxide, barium sulfate, gold, tungsten, or platinum.

In certain embodiments, the outer plunger head is configured to rotate within the internal housing chamber of the fluid housing, and includes at least one scraper element dimensioned to contact an inner housing wall of the fluid housing during rotational movement of the outer plunger head within the internal housing chamber to facilitate displacement of the contrast agent relative to the inner housing wall.

In some embodiments, a clamp retains the outer plunger in the second distal position. The clamp is removable to permit movement of the outer plunger to the first proximal position. The clamp may include first and second end restraints interconnected by a connecting member. The first end restraint can be positioned about a flange of the fluid housing and the second end restraint can be positioned about an outer plunger grip of the outer plunger.

In some embodiments, an end cap is releasably mounted to the fluid housing to enclose the fluid outlet. The end cap may include a cap body which is positionable about a fluid nozzle of the fluid housing and a pin extending from the cap body. The pin is configured to be received within the fluid outlet to close the fluid outlet.

The disclosure also describes a mixing syringe comprising a fluid housing, an outer plunger, and an inner plunger. The fluid housing defines a longitudinal axis and has proximal and distal ends. In addition, the fluid housing defines an internal housing chamber configured to receive a medical agent, and a fluid outlet in communication with the internal housing chamber. The outer plunger is disposed within the internal housing chamber of the fluid housing, and comprises an outer barrel defining a barrel cavity, and an outer plunger head connected to the outer barrel. The outer plunger is configured for longitudinal movement within the internal housing chamber of the fluid housing between a proximal position and a distal position. In addition, the outer plunger head defines a flow passage in communication with the barrel cavity. The outer plunger is configured such that, upon movement of the outer plunger toward the distal position, the medical agent passes from the internal housing chamber through the flow passage into the barrel cavity of the outer plunger. The inner plunger is at least partially disposed within the barrel cavity of the outer plunger, and comprises an inner plunger barrel, and an inner plunger head connected to the inner plunger barrel. The inner plunger is configured for longitudinal movement between a retracted position and an advanced position relative to the outer plunger. With the outer plunger in the distal position and the medical agent disposed in the barrel cavity of the outer plunger, movement of the inner plunger toward the advanced position causes the inner plunger head to force the medical agent through the flow passage of the outer plunger head for disposition through the fluid outlet of the fluid housing.

In some embodiments, the outer plunger head is configured to rotate within the internal housing chamber of the fluid housing, and includes at least one scraper element dimensioned to scrape an inner housing wall of the fluid housing as the outer plunger head rotates relative to the internal housing chamber.

In some embodiments, the outer plunger head is dimensioned to establish a substantial fluid tight seal with an inner housing wall of the fluid housing and the inner plunger head dimensioned to establish a substantial fluid tight seal with an inner barrel wall of the outer plunger.

The syringe may further comprise an end cap configured to be releasably mounted to the fluid housing to enclose the fluid outlet.

The disclosure also describe a method, e.g., for delivering a medical agent to a subject. The method comprises advancing an outer plunger within an internal housing chamber defined by a fluid housing of a syringe such that a medical agent in the internal housing chamber passes through a flow passage defined by an outer plunger head of the outer plunger and into a cavity defined by the outer plunger, and moving an inner plunger through the cavity of the outer plunger to direct the medical agent back through the flow passage for delivery through a fluid outlet of the fluid housing, the fluid outlet being in communication with the internal housing chamber.

The method may include positioning the outer plunger in a distal position such that a volume of the medical agent is stored within the outer barrel, and, thereafter, retracting the outer plunger to a proximal position such that the volume of the medical agent is disposed within the internal housing chamber of the fluid housing. Advancing the outer plunger within the internal housing chamber may comprise advancing the outer plunger after retracting the outer plunger to the proximal position.

In some embodiments, the method includes releasably securing the outer barrel in the distal position. Releasably securing may include mounting a clamp to the fluid housing and the outer plunger.

In some embodiments, the medical agent is a liquid embolic composition. The liquid embolic composition includes a water insoluble contrast agent, and advancing the outer plunger at least partially mixes the contrast agent within the liquid embolic composition.

In some embodiments, rotating the outer plunger head within the internal housing chamber of the fluid housing facilitates mixing of the contrast agent within the liquid embolic composition. In some embodiments, the outer plunger head includes at least one wiper element and wherein rotating the outer plunger head causes the at least one wiper element to displace the contrast agent relative to a housing wall of the fluid housing.

The present disclosure is also directed a method of making a medical syringe. In addition, the method may further comprise introducing a medical agent into the internal housing chamber defined by the fluid housing of the syringe.

The mixing syringe described herein is adapted to uniformly mix a medical agent such as a liquid embolic composition containing a contrast agent and deliver the mixed composition to a catheter or conduit accessing, e.g., the vasculature of a subject. The outer plunger head with scraper elements may help remove any residual contrast agent from the walls of the fluid housing and uniformly mix the components within the apparatus prior to delivery to a catheter. In some examples, the mixing syringe can be pre-filled with the liquid embolic composition, thereby eliminating the need to mix the components prior to the procedure, which helps avoid spills that may occur during the mixing stage and may help reduce treatment time and maximize clinician efficiency.

DETAILED DESCRIPTION

Particular embodiments of the present disclosure are described below with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure. Like reference numerals may refer to similar or identical elements throughout the description of the figures.

FIGS. 1-4 illustrate an example mixing syringe 10. Although the mixing syringe 10 will be discussed in the context of delivering a liquid embolic composition having two or more components, including liquid and/or solid components, to the vasculature of a subject, the mixing syringe 10 may deliver any suitable medical agent or composition, such as any suitable medical agent or composition for treatment of blood vessels, aneurysms, arteriovenous malformations ("AVMs"), arteriovenous fistula ("AVF"), abdominal aortic aneurysm Type 1 and Type 2 endoleaks, portal vein embolization, bleeding, tumors (including hypervascular tumors), or varicose seals, as well as any medical agent or composition for the sterilization of mammals or for the treatment of urinary incontinence.

Figure 3:
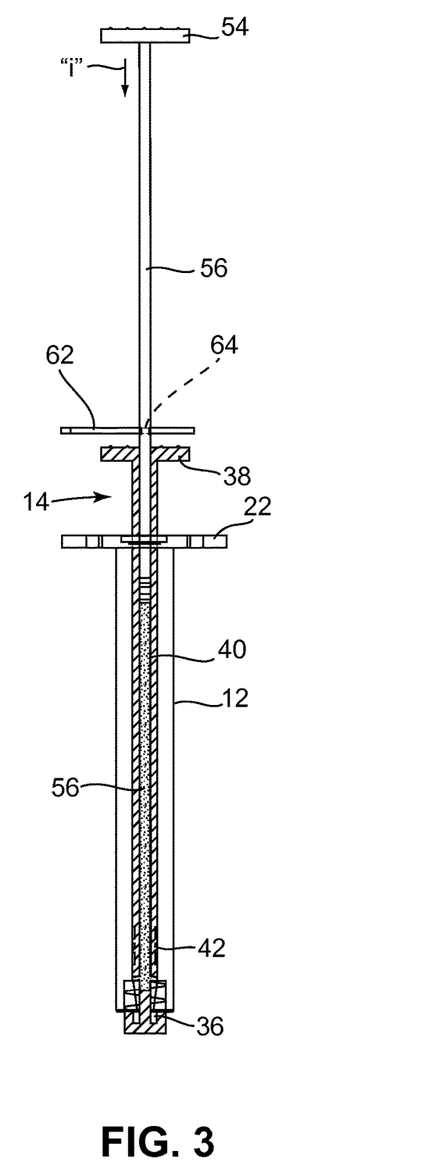
FIG. 3 is a side elevation view in partial cross-section illustrating the mixing syringe of FIG. 1 in a transport condition and containing a liquid embolic composition.
Figure 4:
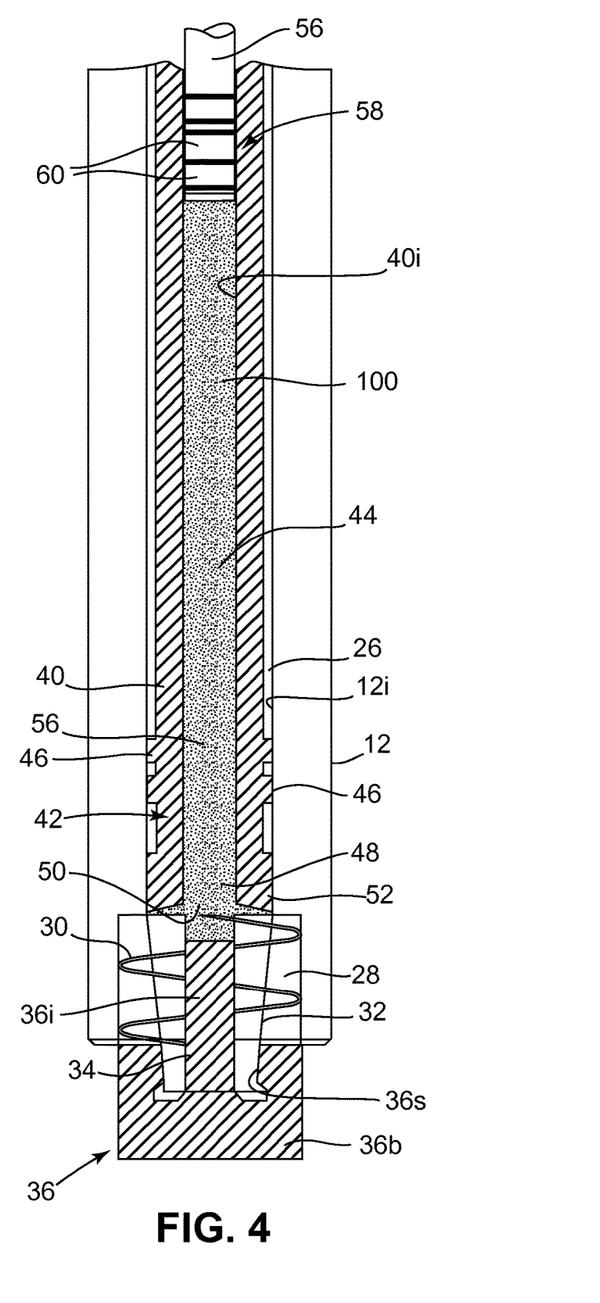
FIG. 4 is an enlarged side elevation view in partial cross-section illustrating the positions of the outer plunger and the inner plunger in the transport condition of FIG. 3.
Figure 5:
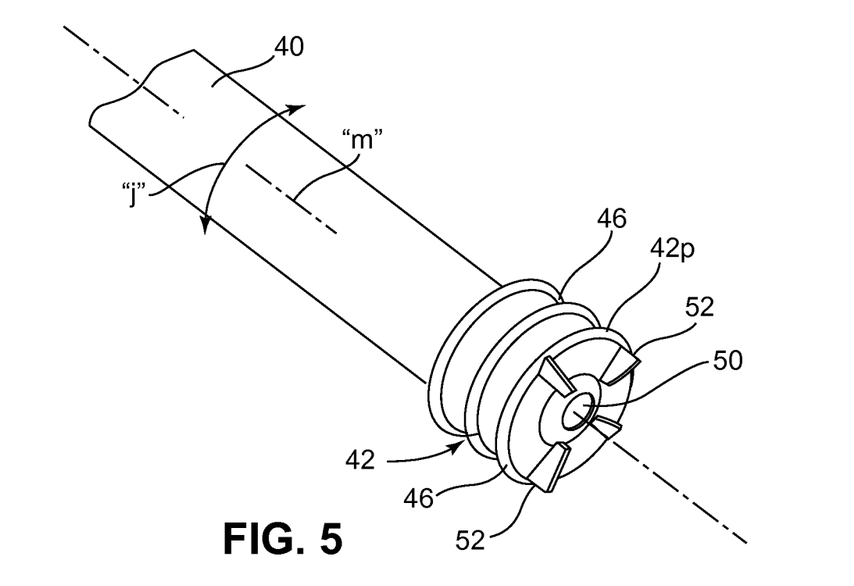
FIG. 5 is a perspective view illustrating the outer plunger head of the outer plunger of FIG. 1.
Figure 6:
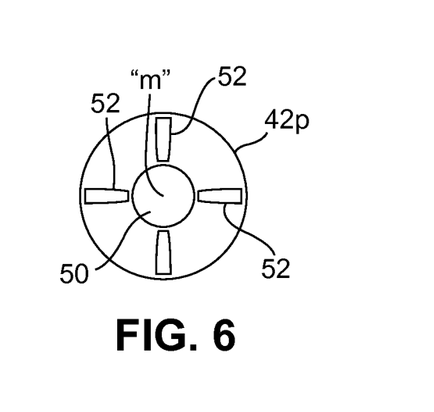
FIG. 6 is an axial view of the outer plunger head of the outer plunger of FIG. 1.

Referring to FIGS. 1-6, the mixing syringe 10 includes a fluid housing 12, an outer plunger 14 at least partially disposed within the fluid housing 12, and an inner plunger 16 which is at least partially disposed within the outer plunger 14. The fluid housing 12 includes an internal housing chamber 26 that at least partially receives the outer and inner plungers 14, 16, and defines a reservoir configured to receive a liquid embolic composition prior to mixing and injecting. The outer plunger 14 includes an outer plunger head 42, which includes a plurality of annular ribs 46 configured to establish a sealing relation with inner wall surface 12i of the fluid housing 12 and at least one or more scraping elements 52 that may extend radially outward to at least the outer perimeter 42p of the outer plunger head 42 as best depicted in FIGS. 5 and 6. The plurality of annular ribs 46 and the scraping elements 52 ensure sufficient mixing of the liquid embolic composition, including the resuspension of any settled contrast agent or contrast agent which has adhered to inner wall surface 12i of the fluid housing 12, to allow immediate injection of a liquid embolic composition with uniformly suspended contrast agent therein.

With reference again to FIGS. 1-4, the mixing syringe 10 includes a fluid housing 12, an outer plunger 14 at least partially disposed within the fluid housing 12, and an inner plunger 16 which is at least partially disposed within the outer plunger 14. The fluid housing 12 defines a longitudinal axis "k" and has a proximal end 18 and a distal end 20. A flange 22 is mounted adjacent the proximal end 18 for engagement by the clinician. The flange 22 may include opposed openings 24 which may receive a suture or ligament to secure the fluid housing 12 relative to a support, the subject, or the outer plunger 14. The fluid housing 12 includes an internal housing chamber 26 terminating adjacent the distal end 20 of the fluid housing 12. The internal housing chamber 26 at least partially receives the outer and inner plungers 14, 16, and also defines a reservoir configured to receive the medical agent during mixing and activation of the outer and inner plungers 14, 16.

Figure 1:
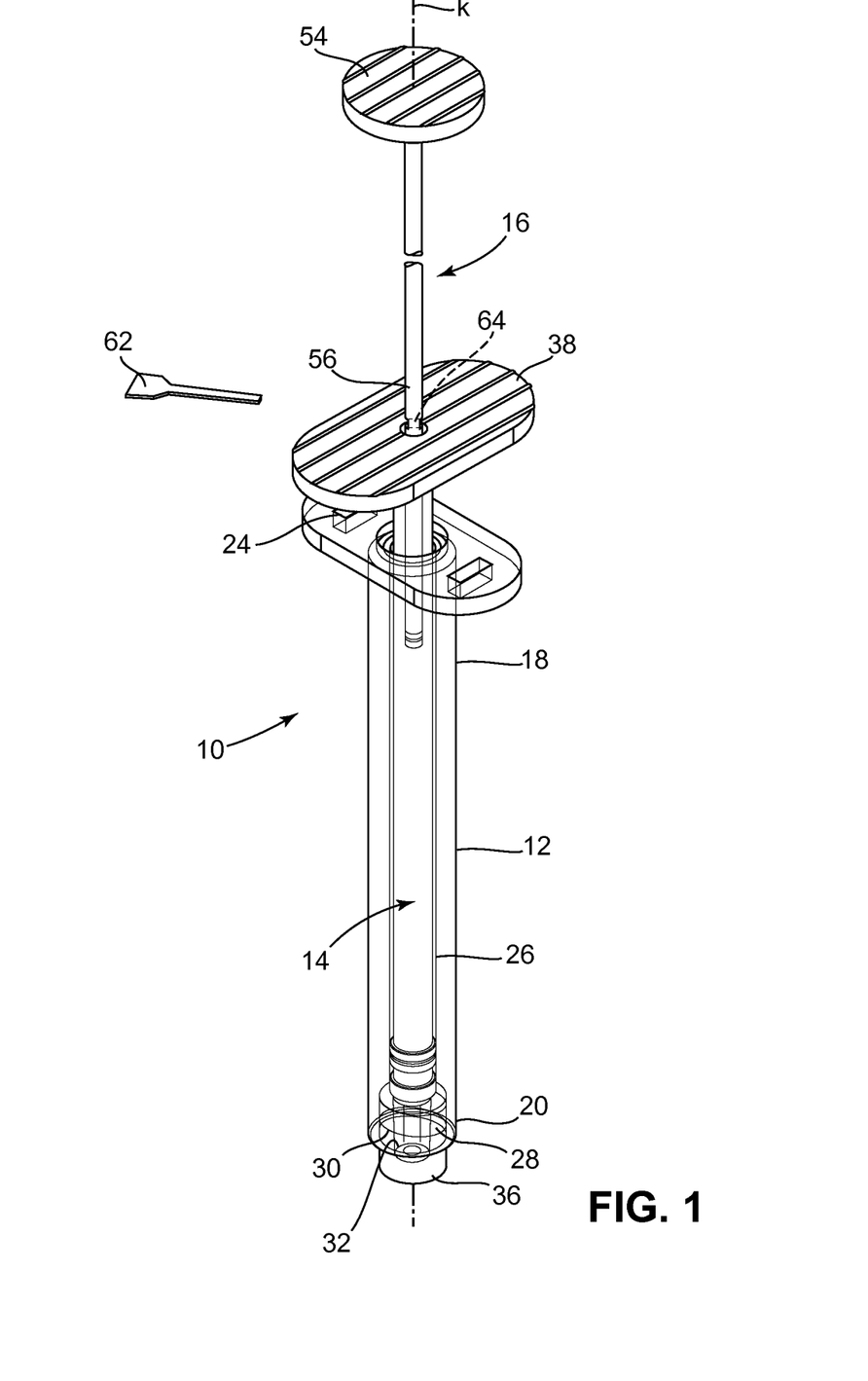
FIG. 1 is a perspective view of an example mixing syringe.
Figure 2:
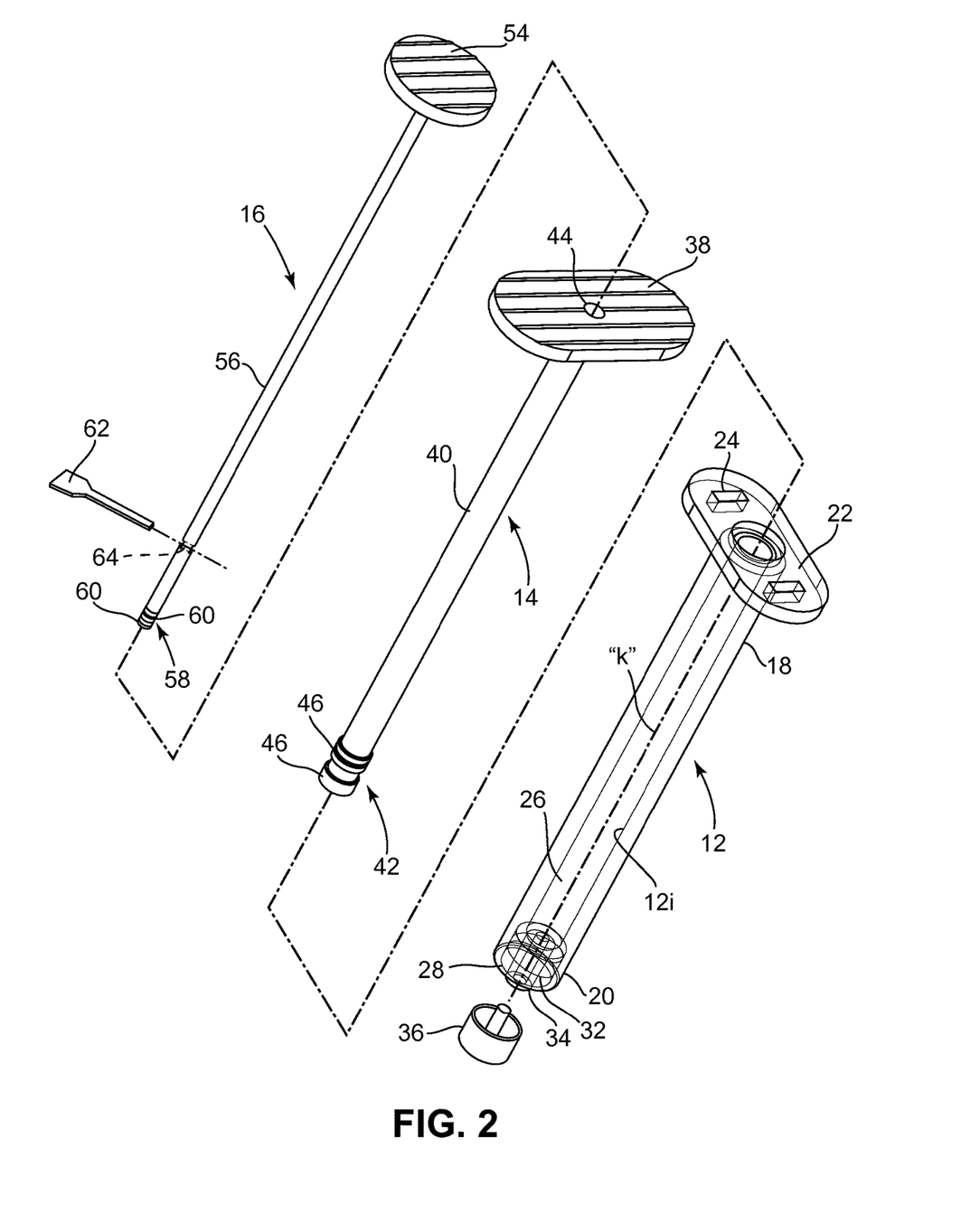
FIG. 2 is an exploded perspective view of the mixing syringe of FIG. 1, illustrating a fluid housing, an outer plunger and an inner plunger.

With reference to FIG. 4, in conjunction with FIGS. 1 and 2, the fluid housing 12 further defines a receptacle 28 at its distal end for reception and/or coupling to a connector associated with a delivery conduit such as a catheter. In one embodiment, the receptacle 28 may have an internal thread 30 configured to cooperate with and mate with a corresponding thread of a luer connector, which is in turn coupled to the catheter. A fluid nozzle 32 extends through the receptacle 28 and defines a fluid outlet 34 in fluid communication with the internal housing chamber 26 for delivering the medical agent into the catheter.

Figure 7:
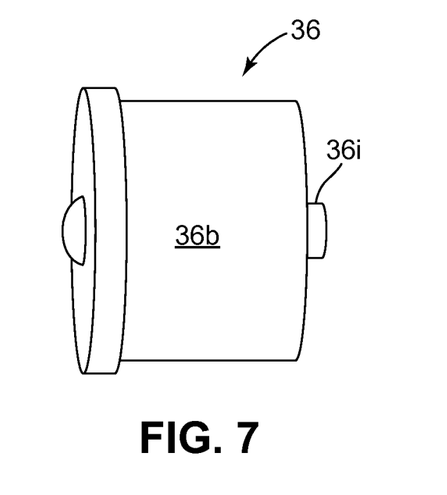
FIG. 7 is a side plan view of an end cap that is mounted to a fluid housing of the mixing syringe shown in FIG. 1.

With reference to FIGS. 2, 4 and 7, an end cap 36 is releasably coupled to the fluid nozzle 32 to contain the medical agent within the internal housing chamber 26 of the fluid housing 12 until the clinician is ready to inject the medical agent. In one embodiment, the end cap 36 is adapted to establish a friction fit with the fluid nozzle 32, e.g., the inner wall surface 36s of the body 36b of the end cap 36 may engage the outer wall of the fluid nozzle 32 in friction relation therewith. In other embodiments, the end cap 36 may include a threaded arrangement that engages the internal thread 30 of the receptacle 28. Other releasable coupling arrangements are also envisioned. In the example shown in FIG. 4, the end cap 36 includes a pin 36i that fills the internal diameter (ID) of the fluid nozzle 32. The pin 36i extends from body 36b and may include an elastomeric material adapted to establish a seal within the fluid nozzle 32. The pin 36i may help prevent settling of contrast agent in the fluid nozzle 32.

Referring again to FIGS. 1-4, the outer plunger 14 includes an outer plunger grip 38, an outer plunger barrel 40, and an outer plunger head 42. The outer plunger head 42 may be monolithically formed with the outer plunger barrel 40, or may be a separate component mounted about the distal end of the outer plunger barrel 40. The outer plunger barrel 40 and the outer plunger head 42 define a barrel cavity 44 extending through these components, which at least partially accommodates or receives the inner plunger 16 (see also FIG. 4). Further, in some examples, the internal diameter (ID) of the outer plunger barrel 40 provides a uniform surface devoid of any areas in which the contrast agent may adhere or settle. The outer plunger 14 is adapted for reciprocal movement (e.g., in a direction parallel to longitudinal axis "k") within the internal housing chamber 26 of the fluid housing 12. The outer plunger 14 also may be configured to rotate within the internal housing chamber 26, such that the outer plunger 14 may be adapted for rotational movement within the internal housing chamber 26.

Referring now to FIGS. 4, 5 and 6, the outer plunger head 42 may define a plurality of outer annular ribs 46, which are dimensioned to establish a sealing relation with the inner wall surface 12i of the fluid housing 12. In one embodiment, one or more of the ribs 46 defines a transverse dimension or diameter generally approximating the internal dimension of the fluid housing 12. The outer plunger head 42, including the annular ribs 46, may be formed of an elastomeric or resilient material such as rubber.

The outer plunger head 42 also includes at least one or more scraper elements 52 extending from the distal end of the outer plunger head 42 dimensioned to contact the inner housing wall 12i of the fluid housing 12 to assist in the mixing of the medical agent. In one embodiment, the outer plunger head 42 includes a plurality of scraper elements 52 arranged in predefined spaced relation about the distal end. For example, the scraper elements 52 may extend radially outwardly relative to a central axis "m" of the outer plunger head 42 toward the outer perimeter 42p of the outer plunger head 42. As best depicted in FIGS. 5 and 6, the scraper elements 52 each may extend radially outward to at least the outer perimeter 42p of the outer plunger head 42. The scraper elements 52 may be linear in configuration, or, in the alternative have an arcuate profile. The scraper elements 52 may define a height, which increases toward the outer perimeter 42p of the outer plunger head 42. The scraper elements 52 may be aligned with the center or central axis "m" of the outer plunger head 42, and may or may not intersect at the central axis "m". In the embodiment shown in FIGS. 5 and 6, the scraper elements 52 terminate at locations radially spaced from the center axis "m" and the distal opening 50.

The scraper elements 52 are formed of an elastomeric or resilient material sufficiently flexible to not interfere with the sealing relation established between the outer plunger head 42 and the inner surface 12i of the fluid housing 12. In an embodiment shown on FIGS. 5 and 6, the scraper elements 52 are monolithically formed with the outer plunger head 42. Four scraper elements 52 are shown and are equidistantly spaced relative to the central axis "m", e.g., at ninety (90) degree intervals. More or less than four scraper elements 52 may be provided.

Referring again to FIGS. 1-4, the inner plunger 16 is at least partially disposed within the barrel cavity 44 of the outer plunger 14. The inner plunger 16 includes an inner plunger grip 54, an inner plunger barrel 56, and an inner plunger head 58. The inner plunger grip 54 may have a different configuration than the outer plunger grip 38 to assist the clinician in distinguishing between the components. The inner plunger head 58 may include a plurality of annular ribs 60 each having a cross-sectional dimension approximating the inner dimension or diameter of the barrel cavity 44. The ribs 60 establish a substantial sealing relation with the inner barrel wall 40i of the outer barrel 40. (FIG. 4).

The inner plunger head 58 may be fabricated from any suitable elastomeric material and connected to the inner plunger barrel 56 through conventional means including mechanical, chemical, or thermal. Alternatively, the inner plunger head 58 may be monolithically formed with inner plunger barrel 56. The inner plunger head 58 is closed at its distal end.

The inner plunger 16 is adapted for reciprocal longitudinal movement relative to the outer plunger 14, i.e., within the barrel cavity 44 of the outer plunger 14 and in a direction substantially parallel to longitudinal axis "k." The inner plunger 16 may be configured to rotate within the barrel cavity 44.

Referring again to FIGS. 1-3, the mixing syringe 10 may also include locking mechanisms to prevent undesired movement of the syringe components prior to delivery of the medical agents, such as during transport or storage. For example, the syringe 10 may include a lock bar 62, which extends through an opening 64 defined by the inner plunger barrel 56 of the inner plunger 16. When disposed within the opening 64, the lock bar 62 engages the outer plunger grip 38 of the outer plunger 14 thereby preventing distal movement (toward distal end 20 of fluid housing 12) of the inner plunger 16 at least relative to the outer plunger 14 and/or proximal movement of the outer plunger 14 relative to the inner plunger 16. The lock bar 62 may be removed during the procedure to permit retracting movement of the outer plunger 14 and advancing movement of the inner plunger 16. Other arrangements for restraining movement of the components of the mixing syringe 10, including the outer plunger 14 relative to the fluid housing 12, can be used, such as the arrangements discussed below.

As indicated hereinabove, in some examples, the mixing syringe 10 may be prefilled with a liquid embolic composition. Suitable liquid embolic compositions to be delivered in the invention are well known. Examples of commonly known liquid embolic compositions are described in U.S. Pat. Nos. 5,694,480; 5,580,568; 5,667,767; and 5,851,508, the entire contents of each of these patents being incorporated by reference herein. Some liquid embolic compositions, such as the ONYX™ liquid embolic system sold by Covidien LP, Irvine, Calif., include a biocompatible polymer such as EVOH (ethylene vinyl alcohol) copolymer, a biocompatible solvent such as DMSO (dimethyl sulfoxide), and a contrast agent suspended therein to provide contrast for visualization under fluoroscopy. Formulations may vary in viscosity, for example, the lower viscosity compositions capable of travelling more distally in the vasculature and capable of penetrating more deeply into the nidus of an aneurysm or malformation.

The water insoluble contrast agents may be in particle or powder form. During treatment, it can be desirable to have the contrast agent in uniform suspension within the liquid embolic composition. However, during storage, these water insoluble contrast agents may settle and, therefore, require sufficient mixing immediately prior to delivery to achieve adequate suspension and resultant ability to visualize the composition under fluoroscopy once delivered to the desired vascular site.

FIGS. 3 and 4 illustrate the mixing syringe 10 in a preferred transport or storage condition with the mixing syringe 10 pre-filled with the liquid embolic composition 100 disposed (or accommodated) within the barrel cavity 44 of the outer plunger 14. In the transport condition, the inner plunger 16 is in a proximally retracted position to leave open the barrel cavity 44 of the outer plunger 14 for the liquid embolic composition 100 to fill. The inner plunger 16 may not move in the distal direction due to the volume of liquid embolic composition 100 within the barrel cavity 44. The outer plunger 14 is in a distal advanced position. As previously disclosed, the end cap 36 and the lock bar 62 facilitate the containment of the liquid embolic composition 100 and restrain movement of the components within the mixing syringe 10 until such time as the clinician is ready to deliver the liquid embolic composition 100. Such a pre-filled configuration can be advantageous to the clinician in reducing procedure preparation time and eliminating spills from the transfer of liquid embolic composition 100 from vial to syringe.

Figure 8:
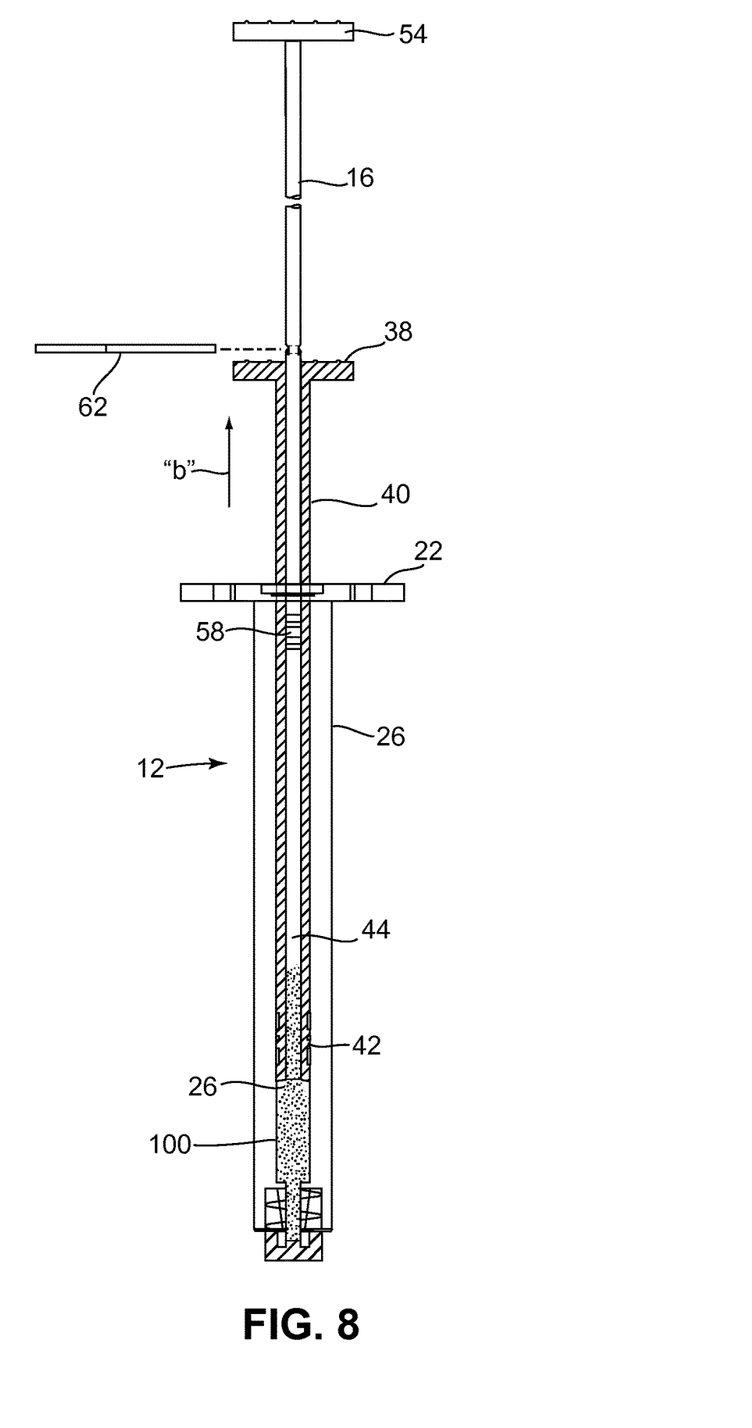
FIG. 8 is a side elevation view in partial cross-section illustrating the outer plunger of the mixing syringe shown in FIG. 1 retracted in accordance with a sequence of steps in use of the mixing syringe for mixing and distributing the liquid embolic composition.
Figure 9:
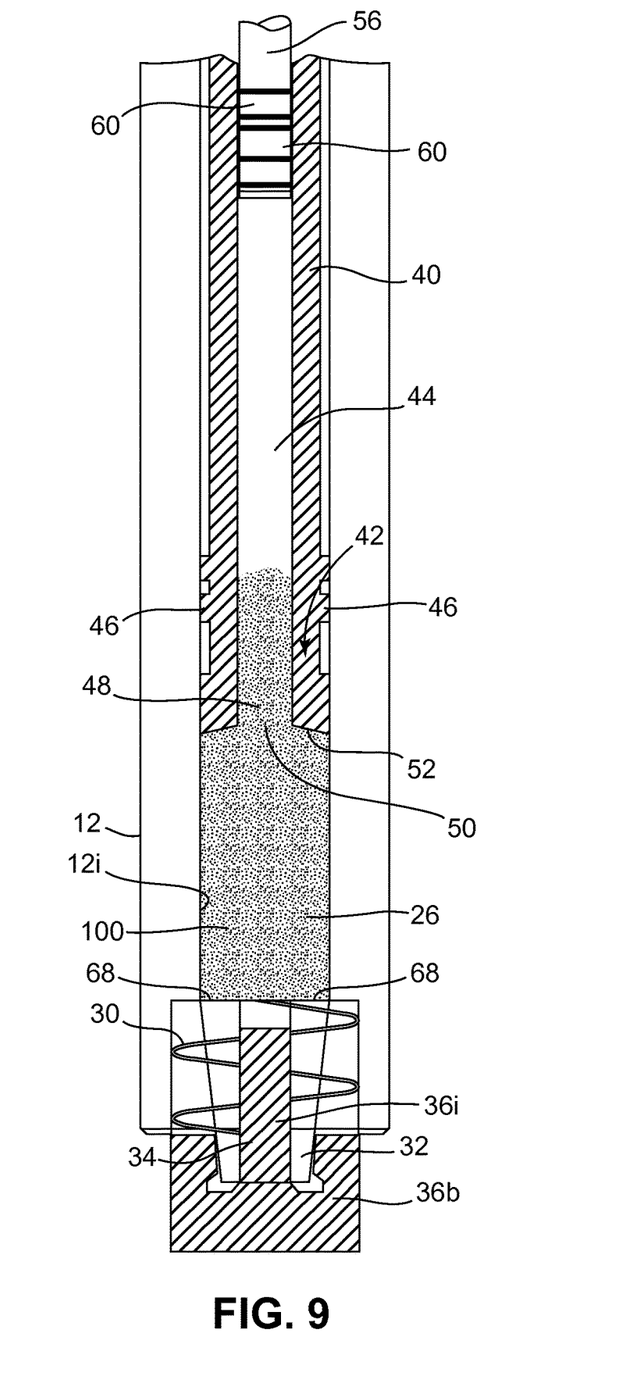
FIG. 9 is an enlarged side elevation view in partial cross-section further illustrating the position of the outer plunger in the retracted position depicted in FIG. 8.

As best depicted on FIG. 8, the lock bar 62 can be removed from the inner plunger barrel 56 of the inner plunger 16 to allow for movement of the outer plunger 14 relative to the inner plunger 16. In one embodiment, the outer plunger 14 is retracted or moved in a proximal direction "b" (FIG. 8) to displace the outer plunger head 42 from the fluid nozzle 32 of the fluid housing 12 creating a void within the internal housing chamber 26 for accommodating a volume of the liquid embolic composition. For example, a volume of the liquid embolic composition 100 is displaced from the barrel cavity 44 of the outer plunger 14 and is accommodated within the internal housing chamber 26 (FIG. 9). The inner plunger 16 may be further retracted in a proximal direction "b" to further open the barrel cavity 44 of the outer plunger 14 if desired.

Figure 10:
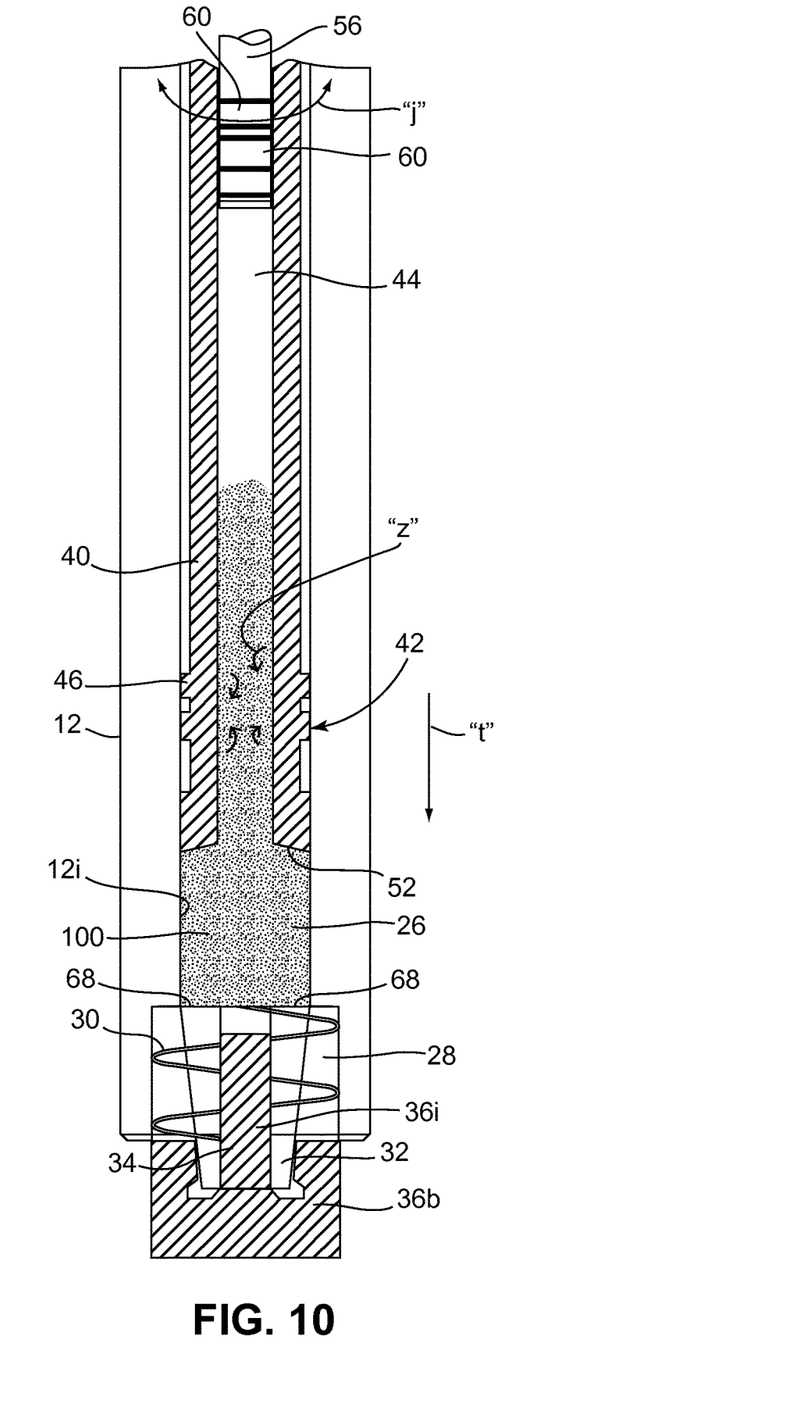
FIG. 10 is a side elevation view in partial cross-section illustrating the outer plunger of the mixing syringe shown in FIG. 1 during advancement within the fluid housing and mixing the liquid embolic composition.

With reference to FIGS. 9 and 10, the procedure is continued by advancing the barrel cavity 44 from a first proximal position (FIG. 9) in the direction of arrow "t" (FIG. 10) causing the outer plunger head 42 of the outer plunger 14 to force the liquid embolic composition 100 into the opening 50 of the outer plunger head 42 for reception within the flow passage 48 of the barrel cavity 44. FIG. 10 illustrates an intermediate position of the outer plunger 14.

The mouth of the flow passage 48 enables the liquid embolic composition 100 to be received within the barrel cavity 44 while minimizing flow resistance.

As the outer plunger head 42 is advanced distally within the internal housing chamber 26, the scraper elements 52 contact the inner wall 12*i* of the fluid housing 12, and scrape any settled or adhered residual contrast agent from the inner wall 12*i*. The contents of the liquid embolic composition 100 including the contrast agent are directed under pressure along a flow pattern leading through the leading opening 50 of the outer plunger head 42, the flow passage 48 and into the barrel cavity 44 of the outer plunger 14 creating sufficient turbulence (identified as arrows "z" in FIG. 10) to ensure the suspension of the contrast agent within the liquid embolic composition 100.

Figure 11:
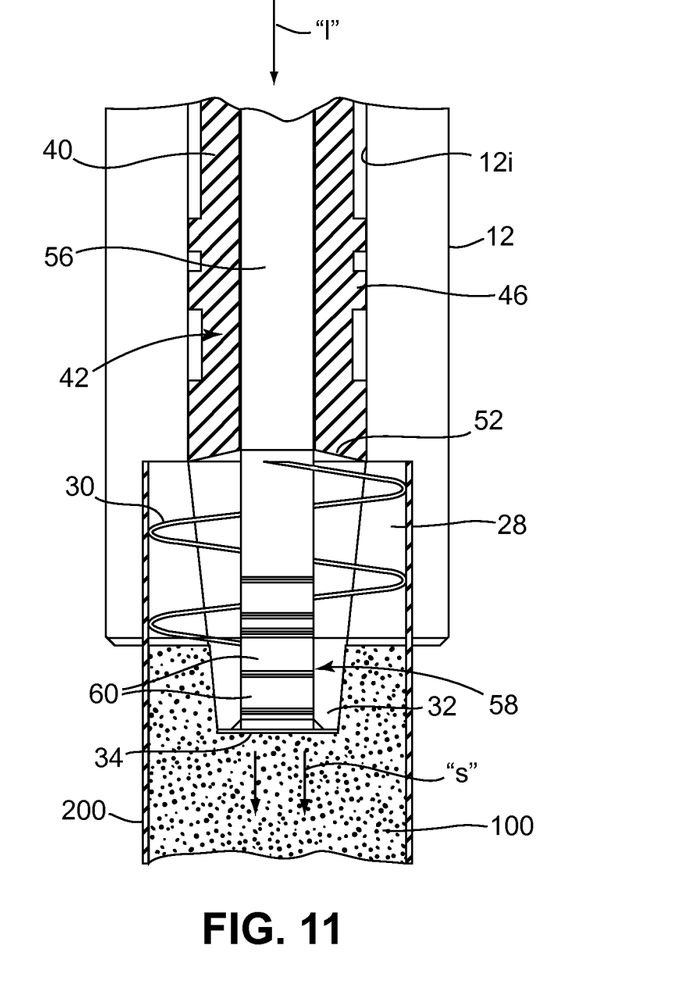
FIG. 11 is an enlarged side elevation view in partial cross-section illustrating the advancement of the inner plunger within the outer plunger of the mixing syringe shown in FIG. 1 for delivering the liquid embolic composition to a catheter accessing a subject.

In addition to the reciprocal movement of each of the inner plunger 16 and the outer plunger 14 within the fluid housing 12, the outer plunger 14 may be rotated about its axis in either direction "j" (FIGS. 5 and 10) to further facilitate removal via the scraper elements 52 of any contrast agent that may have settled or may have adhered to the inner wall 12*i* of the fluid housing 12. Further, the outer plunger 14 also may be rotated when in its second distal or advanced position of FIG. 11 such that the scraper elements 52 engage the forward internal end face 68 (FIG. 10) within the internal housing chamber 26 to remove any contrast agent attached to the forward end face 68 (FIG. 11). The outer plunger 14 may be advanced, retracted and rotated several times to ensure that the scraper elements 52 releases all the residual contrast agent particles from the inner wall 12*i* and the end face 68 of the fluid housing 12. Preferably, the clinician repeats advancement and retraction of the outer plunger 14 at least three (3) times prior to delivery of the medical agent Referring now to FIG. 11, when the clinician is ready to deliver the liquid embolic composition 100 from the mixing syringe 10, the end cap 36 is removed from the fluid nozzle 32. A luer connector 200 is coupled to the receptacle 28. The luer connector 200 is coupled to a catheter placed at the desired treatment site within the vasculature.

The process is continued by advancing the inner plunger 16 in the direction of arrow "l" from the retracted position (FIG. 10) through the barrel cavity 44 to the distal position (FIG. 11) such that the inner plunger head 58 drives the liquid composition 100 through the fluid outlet 34 of the fluid nozzle 32 under pressure for passage to the catheter, and delivery to the targeted vascular treatment site. Upon passage of the liquid embolic composition 100 through the fluid nozzle 32 under pressure, the contrast agent is further mixed within the liquid embolic composition 100 thereby further uniformly suspending the contrast agent within the liquid embolic composition 100.

Figure 12:
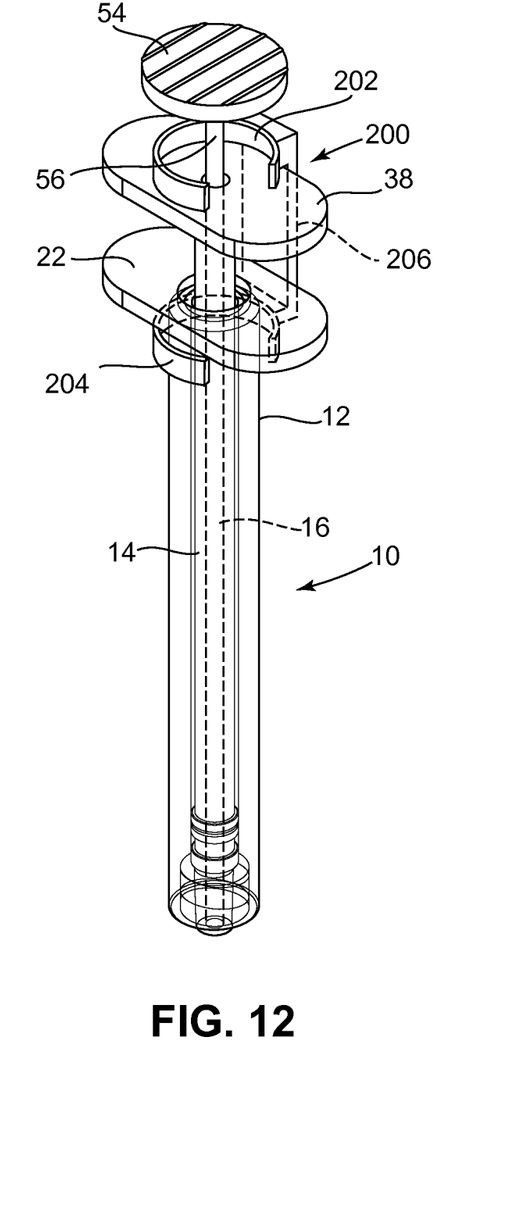
FIG. 12 is a perspective view illustrating a clamp utilized to maintain the outer plunger of the mixing syringe shown in FIG. 1 in a transport condition relative to the fluid housing.

FIG. 12 illustrates another embodiment of the mixing syringe 10. In this embodiment, the mixing syringe 10 includes a fastener, such as a clamp 200, which restrains movement of the outer plunger 14 relative to the fluid housing 12. The clamp 200 may include, opposed end restraints 202, 204 interconnected by connecting member 206. The end restraints 202, 204 may be generally c-shaped and positioned over the respective plunger grip 38 of the outer plunger 14 and the flange 22 of the fluid housing 12. With this arrangement, the outer plunger 14 is restricted from moving, e.g., in the proximal direction, relative to the fluid housing 12 thereby maintaining the volume of liquid embolic composition within the barrel cavity 44 of the outer plunger 14 and preventing preloading of the liquid embolic composition within the internal housing chamber 26 of the fluid housing 12. The clamp 200 may be removed prior to retraction of the outer plunger 14 which movement is shown in FIG. 8. Once the outer plunger 14 is distally advanced to the distal position of FIG. 11, the clamp 200 may be reinstalled or mounted about the plunger grip 38 of the outer plunger 14 and the flange 22 of the fluid housing 12. The inner plunger 16 is advanced to distribute the liquid embolic composition 100. The clamp 200, when installed, will prevent movement of the outer plunger 14 in the proximal direction, which may otherwise occur, in response to the volumetric forces of the liquid embolic composition 100 against the outer plunger head 42, i.e., realized during advancing distal movement of the inner plunger 16. Thus, the clinician does not need to hold the outer plunger 14 to maintain the outer plunger 14 in the distal position during advancement of the inner plunger 16.

In another embodiment, the syringe 10 is not prefilled with a liquid embolic composition 100, but may be filled just prior to application to the subject. For example, the end cap 36 may be removed from the empty syringe 10 and the liquid embolic composition 100 delivered through the fluid nozzle 32 of the fluid housing 12 for reception within the barrel cavity 44 of the outer plunger 14. The syringe 10 may be used in the aforedescribed manner.

In some examples, a method of making any of the mixing syringes described herein may include positioning the outer plunger 14 in the fluid housing 12 of the syringe 10, and positioning the inner plunger 14 in the outer plunger barrel 40. This may be performed in any suitable order. The method may further comprise introducing the liquid embolic composition 100 or another suitable fluid (e.g., another medical agent) in the fluid housing 12. In some examples, the method may further comprise coupling the end cap 36 to the fluid nozzle 32 to help contain the liquid embolic composition 100 within internal housing chamber 26.

In some examples, the method may further comprise fixing a position of the outer plunger 14 relative to the fluid housing 12, e.g., using the lock bar 62, the clamp 200, or another suitable technique.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A mixing syringe comprising:
    a fluid housing defining an internal housing chamber and a fluid outlet in communication with the internal housing chamber;
    an outer plunger defining a cavity and comprising an outer plunger head; and
    an inner plunger,
    wherein, when the mixing syringe is assembled, the outer plunger is disposed within the internal housing chamber of the fluid housing and is configured to move relative to the fluid housing between a proximal position and a distal position, the outer plunger head defining a flow passage between the cavity and the internal housing chamber, the inner plunger is at least partially disposed within the cavity defined by the outer plunger, the inner plunger being configured to move between a retracted position and an advanced position relative to the outer plunger, and the outer plunger and the inner plunger are configured for reciprocal movement relative to each other, wherein the outer plunger head includes a plurality of scraper elements, each scraper element of the plurality defining a surface that contacts an inner housing wall of the fluid housing when the mixing syringe is assembled, wherein the surfaces of the plurality of scraper elements are separated from each other in a direction traverse to a longitudinal axis of the fluid housing, whereby, when the outer plunger is in the distal position and fluid is disposed in the cavity of the outer plunger, movement of the inner plunger toward the advanced position causes the inner plunger to force the fluid through the flow passage of the outer plunger head and through the fluid outlet of the fluid housing.

2. The mixing syringe of claim 1, wherein the outer plunger comprises an outer barrel defining the cavity, the outer plunger head being connected to the outer barrel, and wherein the inner plunger comprises an inner plunger barrel and an inner plunger head connected to the inner plunger barrel.

3. The mixing syringe of claim 1, wherein the outer plunger head is configured to rotate within the internal housing chamber of the fluid housing.

4. The mixing syringe of claim 1 wherein each scraper element of the plurality of scraper elements is dimensioned to extend to an outer periphery of the outer plunger head.

5. The mixing syringe of claim 1, wherein the outer plunger head is dimensioned to establish a substantial fluid tight seal with the inner housing wall of the fluid housing.

6. The mixing syringe of claim 5, wherein the inner plunger comprises an inner plunger head dimensioned to establish a substantial fluid tight seal with an inner barrel wall of the outer plunger.

7. The mixing syringe of claim 1, further comprising the fluid disposed within the internal housing chamber.

8. The mixing syringe of claim 7, wherein the fluid is a liquid embolic composition including a contrast agent.

9. The mixing syringe of claim 8, wherein the contrast agent is water insoluble.

10. The mixing syringe of claim 9, wherein the outer plunger head is configured to rotate within the internal housing chamber of the fluid housing, and wherein each scraper element of the plurality of scraper elements is dimensioned to contact the inner housing wall of the fluid housing during rotational movement of the outer plunger head within the internal housing chamber to facilitate displacement of the contrast agent relative to the inner housing wall.

11. The mixing syringe of claim 8, wherein the contrast agent includes at least one of: tantalum, tantalum oxide, barium sulfate, gold, tungsten, or platinum.

12. The mixing syringe of claim 1, further comprising a clamp configured to retain the outer plunger in the distal position, the clamp being removable to permit movement of the outer plunger to the proximal position.

13. The mixing syringe of claim 12, wherein the clamp includes first and second end restraints interconnected by a connecting member, the first end restraint being positioned about a flange of the fluid housing and the second end restraint being positioned about an outer plunger grip of the outer plunger.

14. The mixing syringe of claim 1, further comprising an end cap configured to be releasably mounted to the fluid housing to enclose the fluid outlet.

15. The mixing syringe of claim 14, wherein the fluid housing includes a fluid nozzle, the fluid nozzle defining the fluid outlet, and wherein the end cap includes an end cap body positionable about the fluid nozzle and a pin extending from the end cap body, the pin being configured to be received within the fluid outlet to close the fluid outlet.

16. A mixing syringe comprising:
a fluid housing defining a longitudinal axis and having proximal and distal ends, the fluid housing defining an internal housing chamber configured to receive a medical agent, and a fluid outlet in communication with the internal housing chamber;
an outer plunger comprising:
an outer barrel defining a barrel cavity; and
an outer plunger head connected to the outer barrel; and
an inner plunger, comprising:
an inner plunger barrel; and
an inner plunger head connected to the inner plunger barrel,
wherein, when the mixing syringe is assembled, the outer plunger is disposed within the internal housing chamber of the fluid housing and configured for longitudinal movement within the internal housing chamber of the fluid housing between a proximal position and a distal position, the outer plunger head defining a flow passage in communication with the barrel cavity, the inner plunger is at least partially disposed within the cavity defined by the outer plunger and is configured for longitudinal movement between a retracted position and an advanced position relative to the outer plunger, and the outer plunger and the inner plunger are configured for reciprocal movement relative to each other, wherein the outer plunger head includes a plurality of scraper elements, each scraper element of the plurality defining a surface that contacts an inner housing wall of the fluid housing when the mixing syringe is assembled, wherein the surfaces of the scraper elements are separated from each other in a direction traverse to the longitudinal axis of the fluid housing,
whereby, with the outer plunger in the distal position and the medical agent disposed in the barrel cavity of the outer plunger, movement of the inner plunger toward the advanced position causes the inner plunger head to force the medical agent through the flow passage of the outer plunger head for disposition through the fluid outlet of the fluid housing.

17. The mixing syringe of claim 16, wherein the outer plunger head is configured to rotate within the internal housing chamber of the fluid housing and each scraper element of the plurality of scraper elements is dimensioned to scrape the inner housing wall of the fluid housing as the outer plunger head rotates relative to the internal housing chamber.

18. The mixing syringe of claim 16, wherein the outer plunger head is dimensioned to establish a substantial fluid tight seal with the inner housing wall of the fluid housing and the inner plunger head is dimensioned to establish a substantial fluid tight seal with an inner barrel wall of the outer plunger.

19. The mixing syringe of claim 16, further comprising an end cap configured to be releasably mounted to the fluid housing to enclose the fluid outlet.

20. The mixing syringe of claim 1, wherein the outer plunger includes an annular rib configured to establish a seal with the inner housing wall of the fluid housing when the mixing syringe is assembled, wherein the plurality of scraper elements are distal to the annular rib.

21. The mixing syringe of claim 1, wherein the plurality of scraper elements extend from a distal end of the outer plunger head.

22. The mixing syringe of claim 1, wherein an axial height of each scraper element of the plurality of scraper elements increases as the scraper element extends out to the surface that contacts the inner housing wall.

\* \* \* \* \*